US009107695B2

(12) United States Patent
Horton et al.

(10) Patent No.: US 9,107,695 B2
(45) Date of Patent: Aug. 18, 2015

(54) SURGICAL INSTRUMENTS AND METHODS OF USE

(71) Applicant: Brolex LLC, Bayshore, NY (US)

(72) Inventors: Jeremy C. Horton, Salt Lake City, UT (US); Steven R. Smith, Draper, UT (US); Kristian J. Olsen, Saratoga Springs, UT (US); Bryce R. Smith, Draper, UT (US)

(73) Assignee: BROLEX LLC, Bayshore, NY (US)

( * ) Notice: Subject to any disclaimer, the term of this patent is extended or adjusted under 35 U.S.C. 154(b) by 278 days.

(21) Appl. No.: 13/839,411

(22) Filed: Mar. 15, 2013

(65) Prior Publication Data

US 2013/0245638 A1   Sep. 19, 2013

Related U.S. Application Data

(60) Provisional application No. 61/612,730, filed on Mar. 19, 2012.

(51) Int. Cl.
*A61B 17/3209* (2006.01)
*A61B 17/42* (2006.01)
*A61B 19/00* (2006.01)
*A61B 17/00* (2006.01)

(52) U.S. Cl.
CPC ........... *A61B 17/42* (2013.01); *A61B 17/32093* (2013.01); *A61B 2017/00424* (2013.01); *A61B 2017/00429* (2013.01); *A61B 2019/461* (2013.01); *A61B 2019/481* (2013.01)

(58) Field of Classification Search
CPC ............... A61B 17/42; A61B 17/4208; A61B 17/3209; A61B 17/32093; A61B 17/3211; A61B 2019/4805; A61B 2019/481
See application file for complete search history.

(56) References Cited

U.S. PATENT DOCUMENTS

| | | |
|---|---|---|
| 893,043 A | 7/1908 | Westerberg |
| 1,192,748 A | 7/1916 | Bundy |
| 1,577,880 A | 3/1926 | Stuart |
| 2,042,273 A | 5/1936 | Okun |
| 2,254,199 A | 9/1941 | Baltuch |
| 2,323,335 A | 7/1943 | Kaye |
| 2,527,201 A | 10/1950 | Silverman |
| 2,610,399 A | 9/1952 | Adams et al. |
| 2,676,595 A | 4/1954 | Dyekjaer |
| 2,724,178 A | 11/1955 | Gensburg |
| 2,743,523 A | 5/1956 | Honey |
| 2,753,105 A | 7/1956 | Werner et al. |
| 2,764,814 A | 10/1956 | Jecker |
| 2,810,194 A | 10/1957 | Unsinger |
| 3,287,751 A | 11/1966 | Hoffman |
| 3,365,798 A | 1/1968 | Cunningham |
| 3,380,159 A | 4/1968 | Winston |
| 3,587,591 A | 6/1971 | Satterwhite |
| 3,624,747 A | 11/1971 | McKnight et al. |
| 3,670,733 A | 6/1972 | Carlisle |
| 3,673,687 A | 7/1972 | Phillips et al. |

(Continued)

*Primary Examiner* — Ryan Severson
(74) *Attorney, Agent, or Firm* — Tarter Krinsky & Drogin LLP

(57) ABSTRACT

A surgical instrument comprises a handle having a blade proximate a distal end of the handle. A blade edge inset from a mouth of the recess is exposed within the recess and faces at least partially toward a proximal end of the handle with the blade edge inset from a mouth of the recess. The distal end further comprises a point bounding a portion of the recess and facing at least partially toward the proximal end of the handle. Methods of use are also disclosed.

26 Claims, 7 Drawing Sheets

(56) References Cited

U.S. PATENT DOCUMENTS

| | | |
|---|---|---|
| 3,751,806 A | 8/1973 | Patrick |
| D230,007 S | 1/1974 | Cramer |
| 3,803,713 A | 4/1974 | Jones et al. |
| 3,835,536 A | 9/1974 | Marcoux |
| 3,877,147 A | 4/1975 | Cummings |
| 4,134,206 A | 1/1979 | Beermann |
| 4,283,853 A | 8/1981 | Fazzini |
| 4,494,542 A | 1/1985 | Lee |
| 4,530,154 A | 7/1985 | Dicarlo |
| 4,604,804 A | 8/1986 | Sparks |
| 4,631,829 A | 12/1986 | Schmidt et al. |
| 4,642,090 A | 2/1987 | Utrata |
| D320,150 S | 9/1991 | Huang |
| 5,046,253 A | 9/1991 | Ireland |
| D323,967 S | 2/1992 | Talbot |
| D327,125 S | 6/1992 | Iten |
| 5,122,152 A | 6/1992 | Mull |
| D332,309 S | 1/1993 | Detsch |
| 5,203,086 A | 4/1993 | Dann |
| 5,285,577 A | 2/1994 | Carney et al. |
| 5,328,026 A | 7/1994 | Newman |
| 5,341,822 A | 8/1994 | Farr et al. |
| D353,316 S | 12/1994 | Schmidt et al. |
| 5,413,580 A | 5/1995 | Stephenson |
| D364,707 S | 11/1995 | Shurtleff |
| 5,487,377 A | 1/1996 | Smith et al. |
| 5,524,348 A | 6/1996 | Tipp |
| 5,555,624 A | 9/1996 | McCracken |
| D381,768 S | 7/1997 | Shurtleff |
| 5,643,311 A | 7/1997 | Smith et al. |
| 5,737,842 A | 4/1998 | Freedman |
| 5,765,289 A | 6/1998 | Schulz et al. |
| 5,768,787 A | 6/1998 | Ireland |
| 5,819,419 A | 10/1998 | Schmidt |
| 5,846,250 A | 12/1998 | Parker |
| 5,884,837 A | 3/1999 | Jacobsson et al. |
| 5,890,290 A | 4/1999 | Davis |
| 5,896,667 A | 4/1999 | Hawkins |
| 5,957,944 A | 9/1999 | Khuri et al. |
| 5,968,055 A | 10/1999 | Dimitriu |
| 6,102,924 A | 8/2000 | Menzin et al. |
| 6,182,364 B1 | 2/2001 | Reyburn |
| 6,267,774 B1 | 7/2001 | Ishii et al. |
| 6,314,644 B1 | 11/2001 | Raeker |
| 6,371,844 B1 | 4/2002 | Holler |
| 6,409,734 B1 | 6/2002 | Zapata |
| D467,658 S | 12/2002 | Goodwin |
| 6,557,258 B1 | 5/2003 | Roberts et al. |
| 6,598,303 B2 | 7/2003 | Bosy et al. |
| 6,619,013 B2 | 9/2003 | Dismukes |
| D481,609 S | 11/2003 | Perlmutter et al. |
| 6,691,416 B2 | 2/2004 | Yu Chen |
| D496,102 S | 9/2004 | Watermeier et al. |
| 6,857,192 B1 | 2/2005 | Summers et al. |
| 6,896,681 B1 | 5/2005 | Watson |
| D514,916 S | 2/2006 | Craig |
| 7,003,884 B2 | 2/2006 | Perlmutter et al. |
| 7,037,255 B2 | 5/2006 | Inman et al. |
| 7,207,999 B2 | 4/2007 | Griffin et al. |
| D573,436 S | 7/2008 | Wu |
| D579,744 S | 11/2008 | Neiser |
| D582,746 S | 12/2008 | Neiser |
| D590,687 S | 4/2009 | Ireland |
| 7,565,747 B2 | 7/2009 | Cobb et al. |
| 7,818,885 B2 | 10/2010 | Lafauci et al. |
| D633,616 S | 3/2011 | Lafauci et al. |
| 7,958,639 B2 | 6/2011 | Ireland |
| 8,112,867 B2 | 2/2012 | Domenico |
| 2002/0194734 A1 | 12/2002 | Huang |
| 2003/0070259 A1 | 4/2003 | Brown et al. |
| 2004/0244206 A1 | 12/2004 | Perlmutter et al. |
| 2005/0044726 A1 | 3/2005 | Summers et al. |
| 2005/0196223 A1 | 9/2005 | Stancovic |
| 2006/0016306 A1 | 1/2006 | Conde |
| 2006/0095057 A1 | 5/2006 | Yi et al. |
| 2008/0243158 A1 | 10/2008 | Morgan |
| 2008/0271323 A1 | 11/2008 | Perlmutter |
| 2009/0198263 A1 | 8/2009 | Lafauci |
| 2010/0234865 A1 | 9/2010 | Lafauci et al. |
| 2011/0106123 A1 † | 5/2011 | Lafauci |

† cited by third party

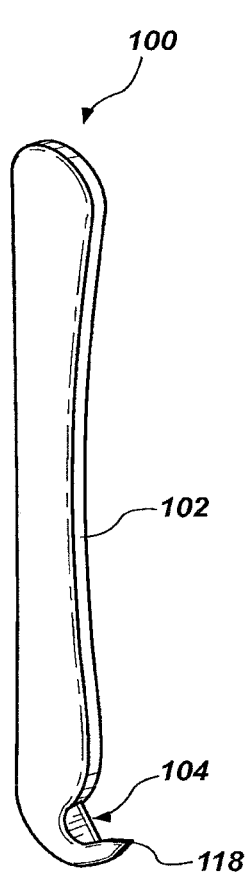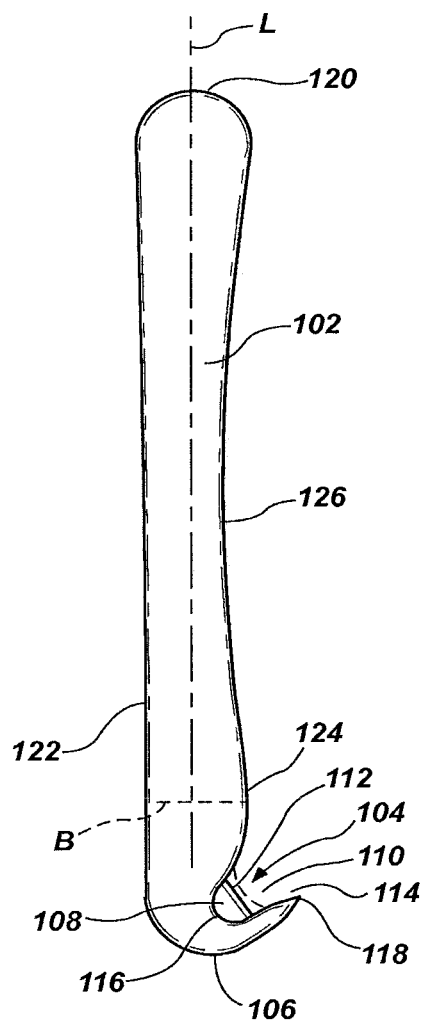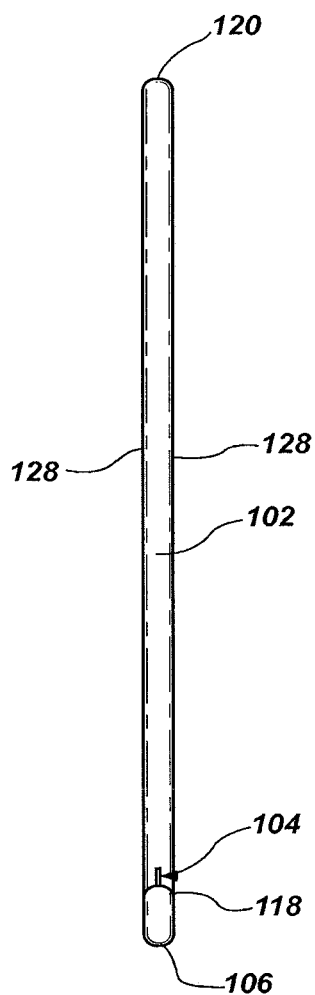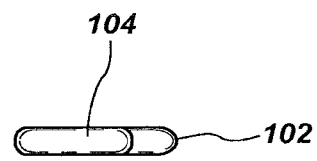
FIG. 1A
FIG. 1B
FIG. 1C
FIG. 1D

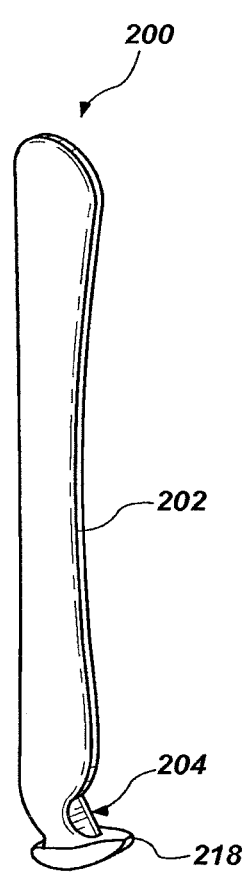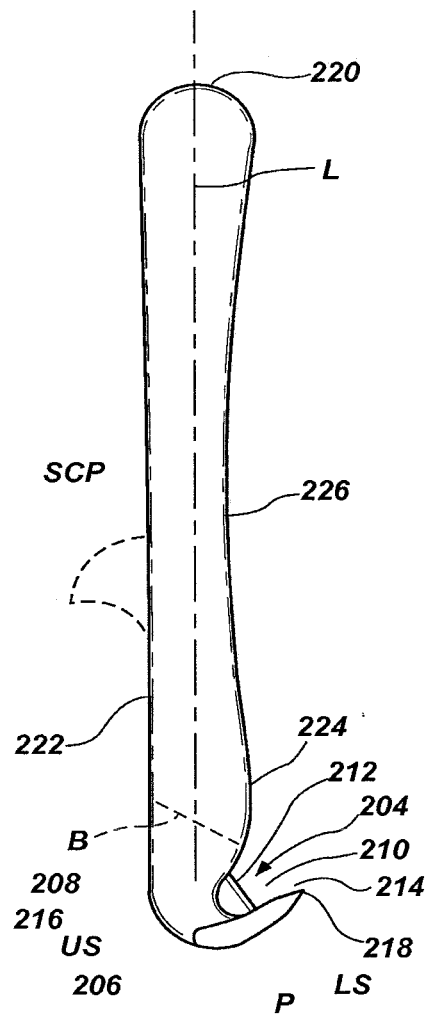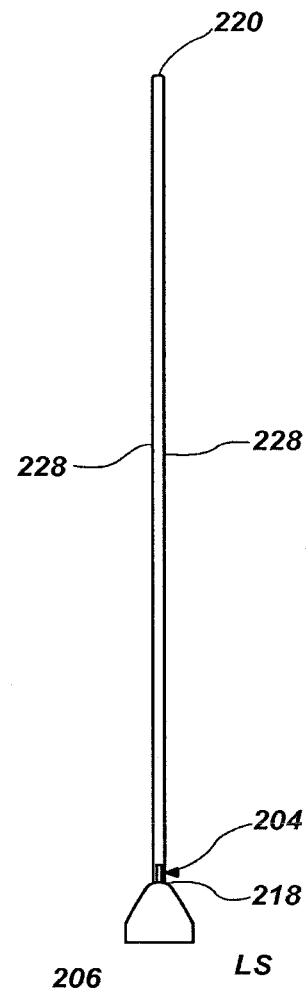
FIG. 2A  FIG. 2B  FIG. 2C
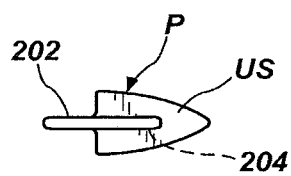
FIG. 2D

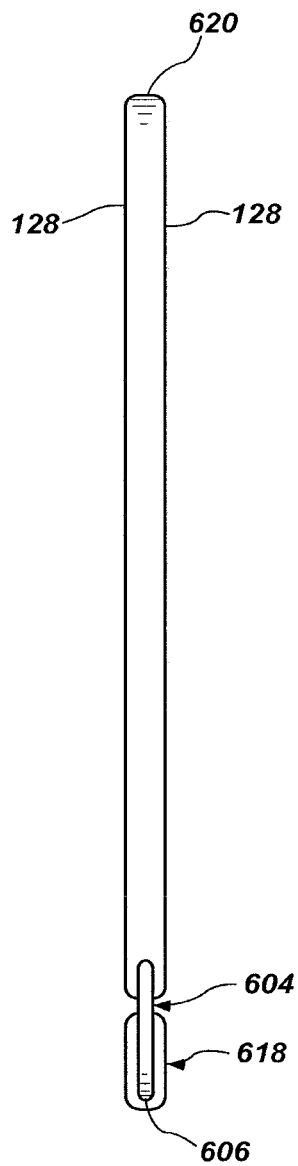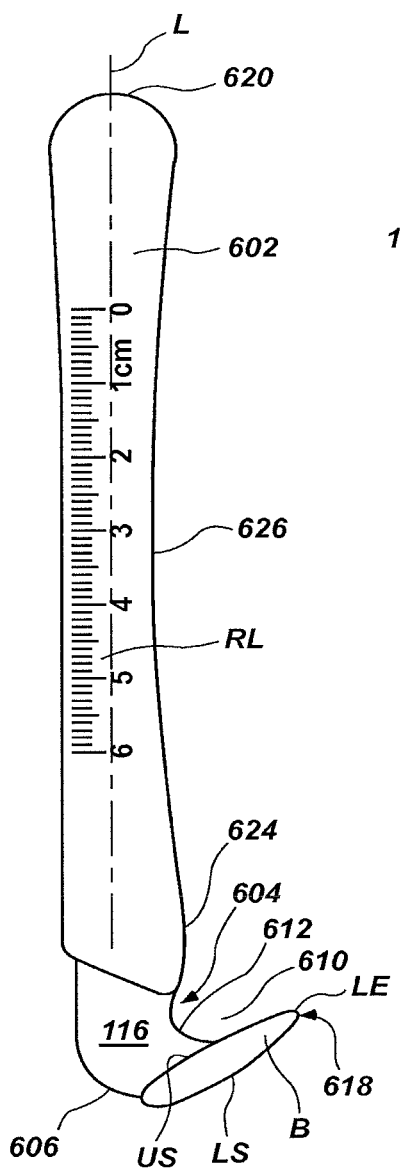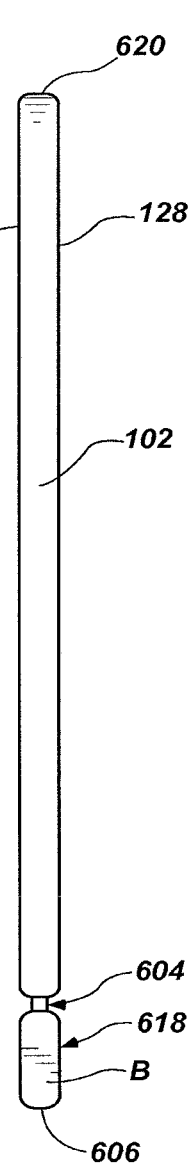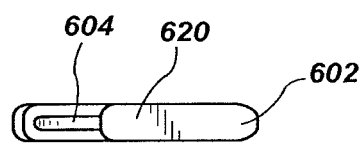
FIG. 6E    FIG. 6B    FIG. 6C
FIG. 6D

SURGICAL INSTRUMENTS AND METHODS OF USE

CROSS-REFERENCE TO RELATED APPLICATION

This application claims the benefit of U.S. Provisional Patent Application Ser. No. 61/612,730 filed Mar. 19, 2012, the disclosure of which is hereby incorporated herein in its entirety by this reference.

TECHNICAL FIELD

Embodiments of the present disclosure relate to surgical instruments and methods of use. More particularly, embodiments of the present disclosure relate to surgical instruments for performing obstetric surgeries including caesarean sections, commonly termed "C-sections," and to methods of manipulating such surgical instruments during the subject surgeries.

BACKGROUND

Obstetric surgeries involve the initiation and completion of one or more incisions, typically as in the case of a caesarean section, through a mother's abdomen (termed a laparotomy) and uterus (termed a hysterotomy) for delivery of one or more babies. Historically, a caesarean section was used as a last resort, in situations when a vaginal delivery was deemed to pose a health risk to the mother or baby. For example, during prolonged labor or a failure to progress to a normal delivery, fetal distress, umbilical cord prolapsed, uterine rupture, hypertension (mother or baby) after amniotic rupture, tachycardia (mother or baby) after amniotic rupture, placental problems, breach or transverse presentation of the baby, failed labor induction, an overly large baby, umbilical cord abnormally, among others. Other complications of pregnancy, preexisting conditions of the mother, and concomitant disease may also indicate the desirability or necessity of a caesarean section.

In recent years, however, caesarean sections have become far more popular, and now comprise a substantial minority of deliveries in the U.S. and abroad. As a consequence, the risks associated with caesarean sections have drawn more attention from the medical community.

In a conventional caesarean section procedure, an abdominal incisions is made, followed by either a midline longitudinal incision in the uterus or, more typically at the present, a lower uterine segment incision. The latter comprises a transverse cut just above the edge of the bladder, and results in less blood loss and facilitates repair, in comparison to the former. In either case, the incisions are typically made with a conventional scalpel, with which the depth of incisions may be difficult to control in some situations, even for a skilled surgeon. In addition, effecting an initial incision requires two acts: first, the scalpel tip is used to perforate the wall of the uterus, followed by reversal of the scalpel in the surgeon's hand to complete the incision. As a consequence, not only is continuity of grip on the scalpel compromised, but also the potential arises for injury to the surgeon, mother and fetus from the scalpel due to a momentary lack of complete control of the instrument.

Attempts to alleviate the aforementioned disadvantages of a conventional scalpel is described in U.S. Pat. No. 7,818,885 to Lafauci et al. Unfortunately, the surgical devices disclosed in the '885 patent require a motion to implement that is foreign to the manner in which surgeons are trained to employ a scalpel. Specifically, not only is a tip, characterized as a "beak," of a surgical device pointed away from the surgeon when an initial tissue perforation is made, but the incision is completed by pushing the surgical device away from the surgeon rather than being drawn toward him or her in a controlled manner and wherein the blade and tissue being incised are more visible.

BRIEF SUMMARY

In one embodiment of the present disclosure, a surgical instrument comprises an elongated handle, a recess proximate a distal end of the handle and facing at least partially toward a proximal end of the elongated handle, a point oriented toward the proximal end of the elongated handle at an acute included angle to a longitudinal axis of the elongated handle and extending along a distal edge of the recess, and a blade having an exposed blade edge facing a mouth of the recess.

In another embodiment, a method of using a surgical instrument comprises perforating tissue in which an incision is to be made using a point on the surgical instrument and elongating the perforation into an incision by drawing the surgical instrument toward the user.

BRIEF DESCRIPTION OF THE DRAWINGS

FIGS. 1A through 1D depict, respectively, an isometric view, a side elevation, a frontal elevation and a proximal end elevation of a first embodiment of the present disclosure;

FIGS. 2A through 2D depict, respectively, an isometric view, a side elevation, a frontal elevation and a proximal end elevation of a second embodiment of the present disclosure;

FIGS. 4A through 4D depict, respectively, an isometric view, a side elevation, a rear elevation and a proximal end elevation of a fourth embodiment of the present disclosure;

FIGS. 5A through 5D depict, respectively, an isometric view, a side elevation, a frontal elevation and a proximal end elevation of a fifth embodiment of the present disclosure; and FIGS. 6A through 6E depict, respectively, an isometric view, a side elevation, a frontal elevation, a proximal end elevation and a rear elevation of a sixth embodiment of the present disclosure.

DETAILED DESCRIPTION

Figures 3A, 3B, 3C:
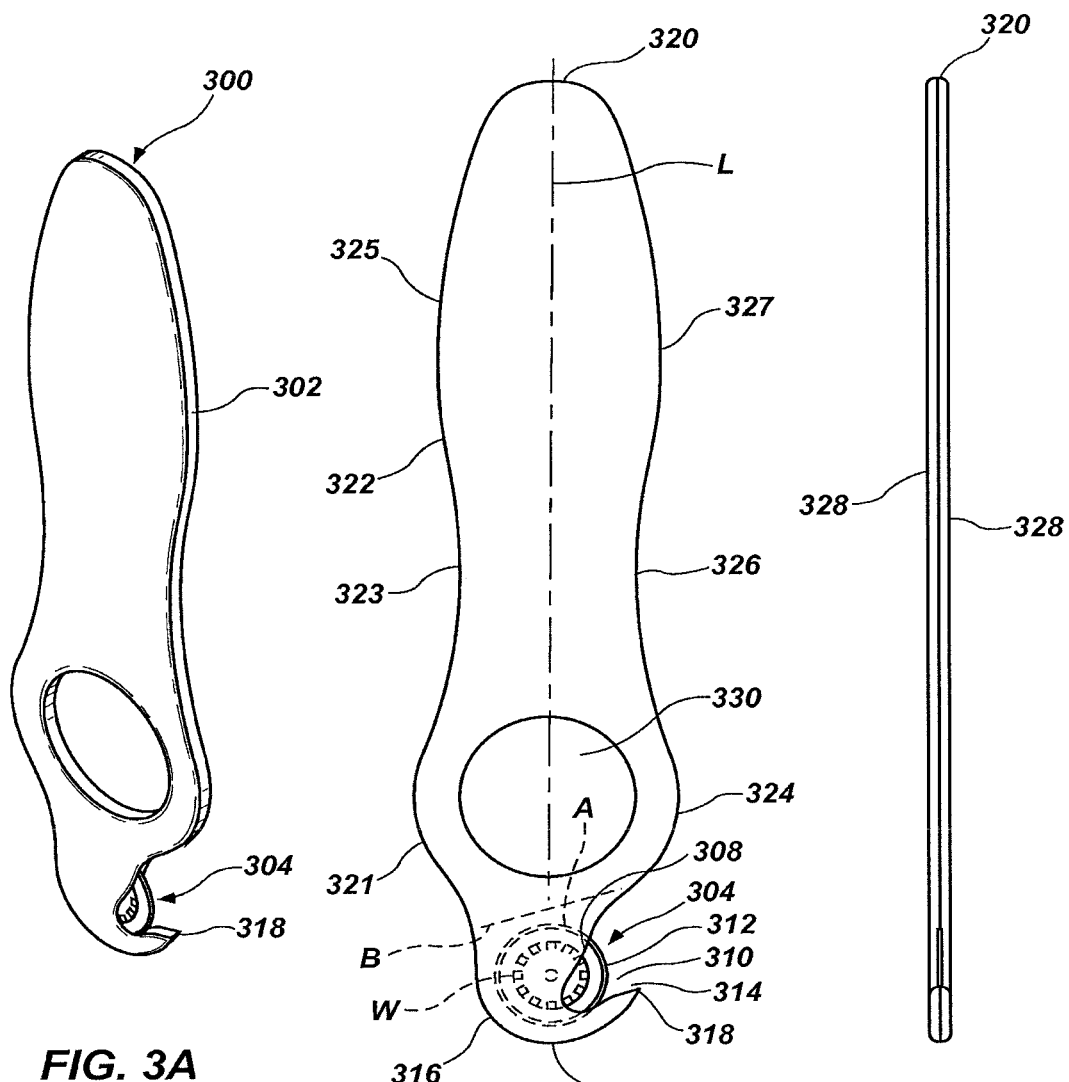
FIGS. 3A through 3D depict, respectively, an isometric view, a side elevation, a frontal elevation and a proximal end elevation of a third embodiment of the present disclosure.
Figure 3D:
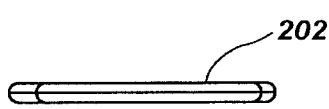
Figure 4D:
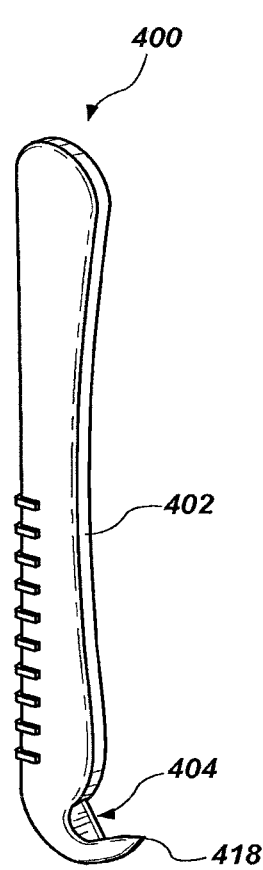
Figure 4D:
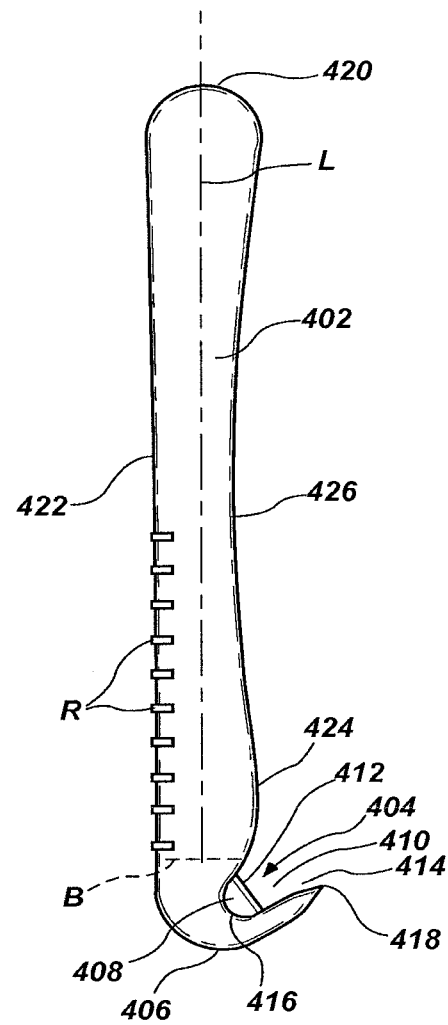
Figure 4D:
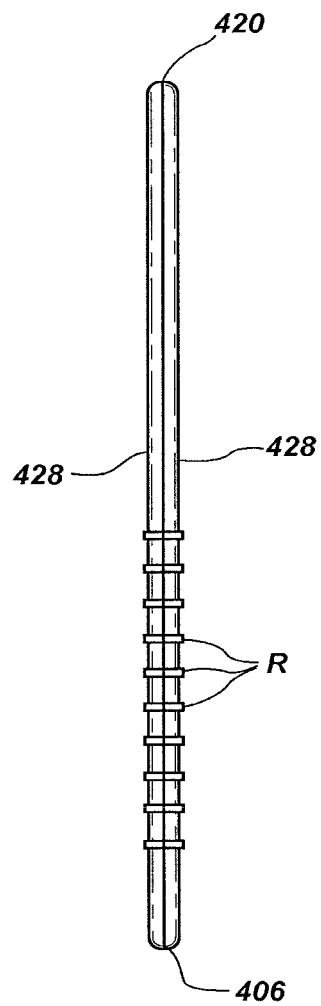
Figure 4D:
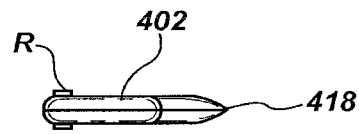
Figure 5D:
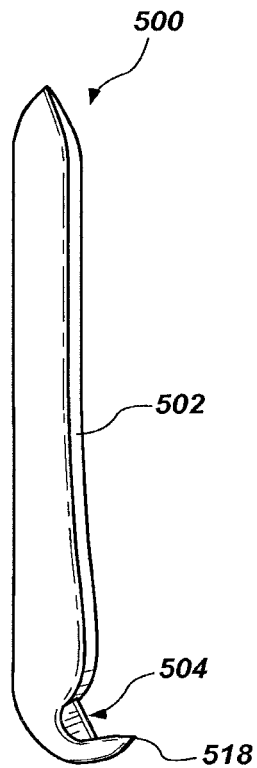
Figure 5D:
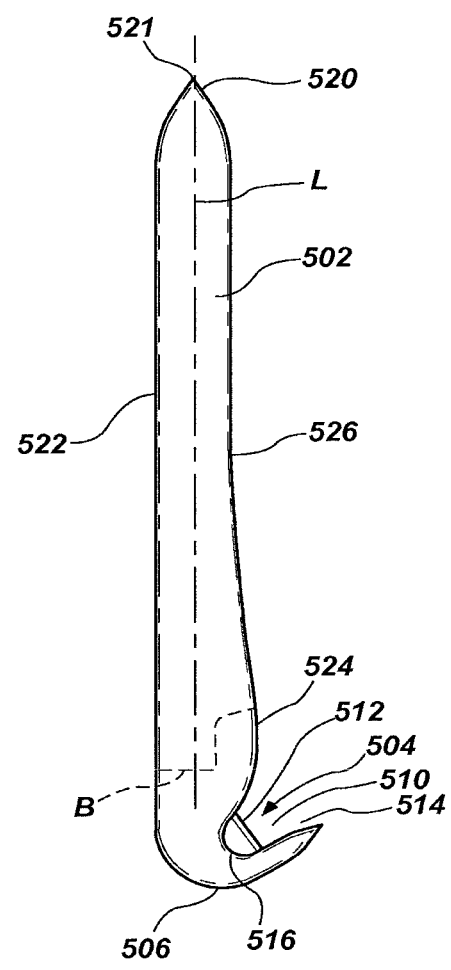
Figure 5D:
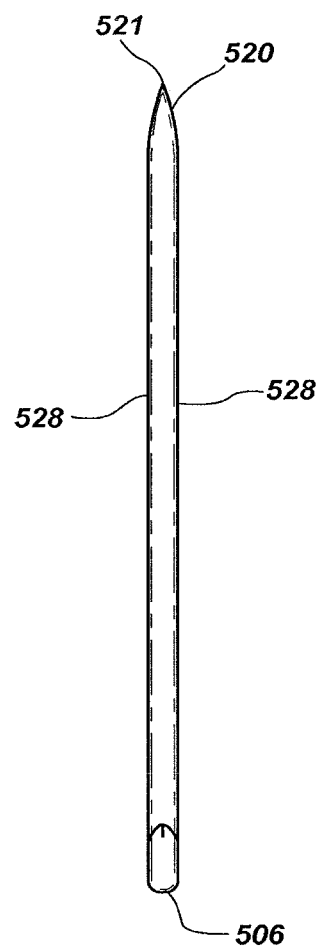
Figure 5D:

The illustrations presented herein are not actual views of any particular surgical instrument, but are merely idealized representations which are employed to describe embodiments of the present disclosure.

FIGS. 1A through 1D depict a first embodiment of a surgical instrument 100 according to the present disclosure. Surgical instrument 100 comprises a handle 102 and a blade 104 secured to handle 102. Handle 102 may comprise a polymer such as polycarbonate, polypropylene, nylon, acrylonitrile butadiene styrene, etc., and be formed by injection molding. Blade 104 may comprise a metal alloy, for example surgical grade stainless steel, and may be secured to handle 102 during the molding process, as is conventional. Blade 104 may be of a width, by way of non-limiting example, of about 0.15 in., or of greater or lesser width. Blade 104 is located near the distal end 106 of handle 102, and a portion 108 of blade 104 is exposed within recess 110, the edge 112 of blade 104 being inset from the mouth 114 of recess 110. As depicted, blade edge 112 is linear, sharp, and lies at an included angle of between about 125° and about 145°, for example about 135°, to longitudinal axis L of handle 102. Recess 110, which faces at least partially toward a proximal end 120 of handle 102, includes an arcuate base 116 and widens therefrom toward mouth 114, opening at an included angle ranging from about 40° to about 60°. Point 118, which is sharp in side elevation (FIG. 1B) and rounded in frontal elevation (FIG. 1C), protrudes at an acute included angle to longitudinal axis L of handle 102 of between about 45° and about 75°, for example about 60°, and is oriented toward proximal end 120 of handle 102. Distal end 106 of handle 102 is rounded, as is proximal end 120. Spine 122 at the back of handle 102 is substantially linear, while the front of handle 102 above recess 110 comprises an arcuate belly 124 bulging outwardly at one side of recess 110 and which recedes into a shallow concavity 126 substantially leading to rounded proximal end 120. Sides 128 of handle 102 are substantially flat, and the transition surfaces between sides 128 and each of distal end 106, proximal end 120 and spine 122 of handle 102 are rounded and devoid of sharp edges. The transition surfaces from each side 128 of handle 102 to meet the sides of blade 104 within recess 110 are also rounded and devoid of sharp edges.

FIGS. 2A through 2D depict a second embodiment of a surgical instrument 200 according to the present disclosure. Surgical instrument 200 comprises a handle 202 and a blade 204 secured to handle 202. Handle 202 may comprise a polymer such as polycarbonate, polypropylene, nylon, acrylonitrile butadiene styrene, etc., and be formed by injection molding. Blade 204 may comprise a metal alloy, for example surgical grade stainless steel, and may be secured to handle 202 during the molding process, as is conventional. Blade 204 may be of a width, by way of non-limiting example, of about 0.15 in., or of greater or lesser width. Blade 204 is located near the distal end 206 of handle 202, and a portion 208 of blade 204 is exposed within recess 210, the edge 212 of blade 204 being inset from the mouth 214 of recess 210. As depicted, blade edge 212 is linear, sharp, and lies at an included angle of between about 125° and about 145°, for example about 135°, to longitudinal axis L of handle 102. Recess 210, which faces at least partially toward a proximal end 220 of handle 202, includes an arcuate base 216 and widens therefrom toward mouth 214, opening at an included angle ranging from about 40° to about 60°. Point 218, which is sharp in side elevation (FIG. 2B) and somewhat rounded in frontal elevation (FIG. 2C), protrudes at an acute included angle to longitudinal axis L of handle 202 of between about 45° and about 55°, for example about 60°, and is oriented toward proximal end 220 of handle 202. Point 218, unlike point 118 of the first embodiment, extends laterally from handle 102 and comprises a plow-shaped body P having a wedge-shaped leading edge W with a substantially flat upper, proximal surface US and a rounded lower, distal surface LS. Distal end 206 of handle 202 is rounded in side elevation, as is proximal end 220. The rounded lower surface LS of plow-shaped body P is contiguous with the remainder of distal end 206, and the trailing edge thereof is rounded, both as depicted in FIG. 2B. Spine 222 at the back of handle 202 is substantially linear, while the front of handle 202 above recess 210 comprises an arcuate belly 224 bulging outwardly at one side of recess 210 and which recedes into a shallow concavity 226 substantially leading to rounded proximal end 220. Sides 228 of handle 202 are substantially flat, and the transitions between sides 228 and each of distal end 206, proximal end 220 and spine 222 of handle 202 are rounded and devoid of sharp edges. The transition surfaces from each side 228 of handle 202 to meet the sides of blade 204 within recess 210 above plow-shaped body P are also rounded and devoid of sharp edges. Substantially flat upper surface S of plow-shaped body P meets the sides of blade 204 at the lower boundary of recess 210 at a substantially perpendicular angle.

FIGS. 3A through 3D depict a third embodiment of a surgical instrument 300 according to the present disclosure. Surgical instrument 300 comprises a handle 302 and a blade 304 secured to handle 302. Handle 302 may comprise a polymer such as polycarbonate, polypropylene, nylon, acrylonitrile butadiene styrene, etc., and be formed by injection molding. Blade 304 is circular as shown in broken lines, and may comprise a metal alloy, for example surgical grade stainless steel, and may be rotatably positioned to move during use with regard to axle A secured to handle 302 during the molding process, as is conventional. For example, blade 304 may be maintained in position for rotation using a male axle protruding from each side of blade 304 and rotationally secured in cooperative recesses in opposing sides of handle 302. Alternatively, a female axle may be secured to opposing sides of handle 302 and extend through a hole in the center of blade 302, or the female axle might be formed of handle material and extend through the hole. To provide clearance for blade rotation, both sides of handle 302 would be formed with shallow recesses adjacent the segment of blade 304 residing within handle 302. Blade 304 is located near the distal end 306 of handle 302, and a portion 308 of blade 304 is exposed within recess 310, the edge 312 of blade 304 being slightly inset from the mouth 314 of recess 310. Blade 304 may be of a width, by way of non-limiting example, of about 0.15 in., or of greater or lesser width. As depicted, exposed blade edge 312 is sharp and convex, comprising a portion of a circle, and the exposed portion will change with blade rotation during use. Recess 310 includes an arcuate base 116 and widens therefrom toward mouth 314, opening at an included angle ranging from about 40° to about 50°. Point 318, which is sharp in side elevation (FIG. 3B) and rounded in frontal elevation (FIG. 3C), protrudes at an acute included angle to longitudinal axis L of handle 302 of between about 45° and about 75°, for example about 60°, and is oriented at least partially toward proximal end 320 of handle 302. Blade 304 is mounted to handle 302 so that blade edge 312 and point 318 together define an acute angle. Distal end 306 of handle 302 is rounded, as is proximal end 320. Spine 322 at the back of handle 302 comprises an arcuate back 321, a contiguous shallow concavity 323, and a shallow convex portion 325 leading to proximal end 320, while the front of handle 302 above recess 310 comprises an arcuate belly 324 bulging outwardly at one side of recess 310 and which recedes into a shallow concavity 326 followed by a shallow convex portion 327 substantially leading to rounded proximal end 320. Sides 328 of handle 302 are substantially flat, and the transition surfaces between sides 328 and each of distal end 306, proximal end 320 and spine 322 of handle 302 are rounded and devoid of sharp edges. The transitions from each side 328 of handle 302 to meet the sides of blade 304 within recess 310 are also rounded and devoid of sharp edges. Aperture 330 extends through handle 302 between arcuate back 321 and arcuate belly 324. In a variation of the third embodiment, as depicted in broken lines in FIG. 3B, a drive wheel W of smaller diameter than a diameter of blade 304 may be disposed on one or both sides of handle 302 and coupled to axle A, which would in this variation be a male axle A secured to blade 304, extending through an aligned aperture in one or preferably both sides of handle 302, and a drive wheel or wheels W would be secured thereto to provide motive force for blade rotation. The outer rim of drive wheel W may be smooth, or may comprise ribs, ridges, grooves, a knurled edge or other textured structure to provide additional frictional force, and thus traction, against the exposed surface of tissue severed by blade 312 as it rotates, to cause positive blade rotation of blade in a clockwise direction (as surgical instrument is oriented in FIG. 3B).

FIGS. 4A through 4D depict a fourth embodiment of a surgical instrument 400 according to the present disclosure. Surgical instrument 400 comprises a handle 402 and a blade 104 secured to handle 402. Handle 402 may comprise a polymer such as polycarbonate, polypropylene, nylon, acrylonitrile butadiene styrene, etc., and be formed by injection molding. Blade 404 may comprise a metal alloy, for example surgical grade stainless steel, and may be secured to handle 402 during the molding process, as is conventional. Blade 404 may be of a width, by way of non-limiting example, of about 0.15 in., or of greater or lesser width. Blade 404 is located near the distal end 406 of handle 402, and a portion 408 of blade 404 is exposed within recess 410, the edge 412 of blade 404 being inset from the mouth 414 of recess 410. As depicted, blade edge 412 is linear, harp, and lies at an included angle of between about 125° and about 145°, for example about 135°, to longitudinal axis L of handle 402. Recess 410, which faces at least partially toward a proximal end 420 of handle 402, includes an arcuate base 416 and widens therefrom toward mouth 414, opening at an included angle ranging from about 40° to about 60°. Point 418, which is sharp in side elevation (FIG. 4B) and rounded in frontal elevation (similar to the structure depicted in FIG. 1B), protrudes at an acute included angle to longitudinal axis L of handle 402 of between about 45° and about 75°, for example about 60°, and is oriented toward proximal end 420 of handle 402. Distal end 406 of handle 402 is rounded, as is proximal end 420. Spine 422 at the back of handle 102 is substantially linear, and is surmounted by a row of ridges, which may also be characterized as ribs, R extending transverse to spine 422 and wrapping over onto sides 428 of handle 401. In one embodiment, the ribs R are spaced to define measurement increments (millimeters, centimeters, etc.) to comprise a ruler, and the handle may, optionally, be marked with units for the measurement increments. Ribs R may also be characterized as a gripping structure to enhance frictional engagement between the spine of the surgical instrument and a digit, for example an index finger, of the surgeon. Other gripping structures, such as knurling or texturing a surface of spine 422, are also contemplated. The front of handle 402 above recess 410 comprises an arcuate belly 424 bulging outwardly at one side of recess 410 and which recedes into a shallow concavity 426 substantially leading to rounded proximal end 420. Sides 428 of handle 402 are substantially flat, and the transition surfaces between sides 428 and each of distal end 406, proximal end 420 and spine 422 of handle 402 are rounded and devoid of sharp edges. The transition surfaces from each side 428 of handle 402 to meet the sides of blade 404 within recess 410 are also rounded and devoid of sharp edges.

FIGS. 5A through 5D depict a fifth embodiment of a surgical instrument 500 according to the present disclosure. Surgical instrument 500 comprises a handle 502 and a blade 504 secured to handle 502. Handle 502 may comprise a polymer such as polycarbonate, polypropylene, nylon, acrylonitrile butadiene styrene, etc., and be formed by injection molding. Blade 504 may comprise a metal alloy, for example surgical grade stainless steel, and may be secured to handle 502 during the molding process, as is conventional. Blade 504 may be of a width, by way of non-limiting example, of about 0.15 in., or of greater or lesser width. Blade 504 is located near the distal end 506 of handle 502, and a portion 508 of blade 504 is exposed within recess 510, the edge 512 of blade 504 being inset from the mouth 514 of recess 510. As depicted, blade edge 512 is linear, sharp, and lies at an included angle of between about 125° and about 145°, for example about 135°, to longitudinal axis L of handle 502. Recess 510, which faces at least partially toward a proximal end 520 of handle 502, includes an arcuate base 516 and widens therefrom toward mouth 514, opening at an included angle ranging from about 40° to about 60°. Point 518, which is sharp in side elevation (FIG. 5B) and rounded in frontal elevation (FIG. 5C), protrudes at an acute included angle to longitudinal axis L of handle 502 of between about 45° and about 75°, for example about 45°, and is oriented toward proximal end 520 of handle 502. Distal end 506 of handle 502 is rounded, while proximal end 520 extends to a point 521. Spine 522 at the back of handle 502 is substantially linear, while the front of handle 502 above recess 510 comprises an arcuate belly 524 bulging outwardly at one side of recess 510 and which recedes into a substantially linearly extending front surface 526 leading to pointed proximal end 520. Sides 528 (one shown) of handle 502 are substantially flat, and the transitions between sides 528 and each of distal end 506 and spine 522 of handle 502 are rounded and devoid of sharp edges. The transitions from each side 528 of handle 502 to meet the sides of blade 504 within recess 510 are also rounded and devoid of sharp edges. However, sides 528, spine 522 and front surface 526 of handle taper inwardly at proximal end 520 to form point 521 of proximal end 520, having otherwise rounded transition surfaces therebetween.

Figure 6A:
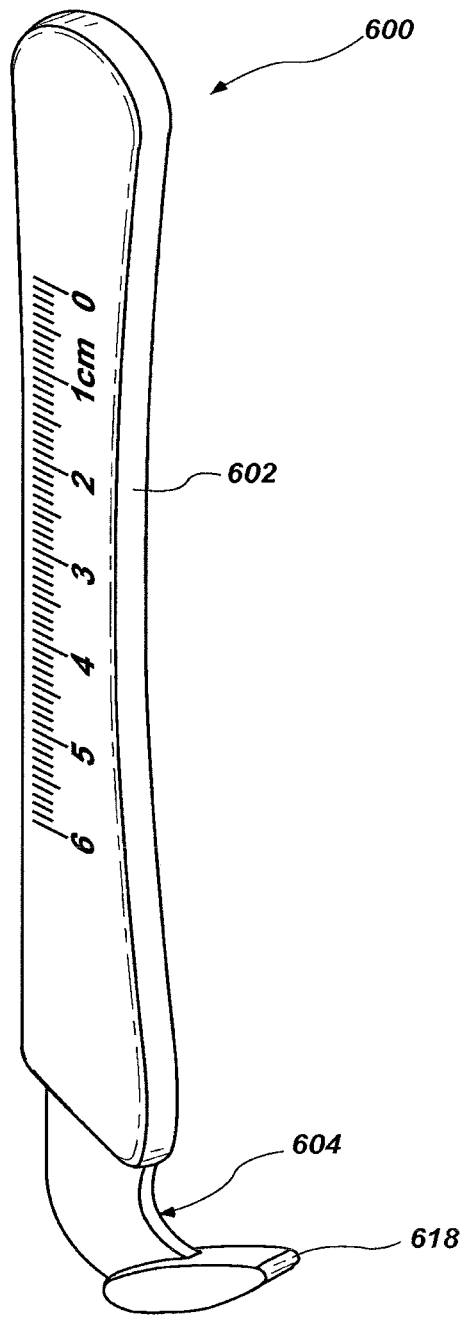

FIGS. 6A through 6E depict a sixth embodiment of a surgical instrument 600 according to the present disclosure. Surgical instrument 600 is somewhat similar in configuration to surgical instrument 200 of the second embodiment. Surgical instrument 600 comprises a handle 602 comprising a blade segment 604. Handle 602 may comprise a polymer such as polycarbonate, polypropylene, nylon, acrylonitrile butadiene styrene, etc., and be formed by injection molding. Blade segment 604 is formed (e.g., molded) integrally with handle 602 and of the same material as handle 602, unlike blade 204 of the second embodiment, which is a separate structure comprising a metal alloy, for example surgical grade stainless steel, secured to handle 202 during the molding process. Blade segment 604 may be of a width, by way of non-limiting example, of about 0.18 in., or of greater or lesser width. Blade segment 604 is located proximate to, and comprises the distal end 606 of, handle 602, and the edge 612 of blade forms an inner boundary, which may also be characterized as a base, of recess 610 inset from the mouth 614 of recess 610. As depicted, blade edge 612 is arcuate (e.g., concave), unsharpened, and lies substantially at an included angle of between about 125° and about 145°, for example about 135°, to longitudinal axis L of handle 602. Recess 610, which faces at least partially toward a proximal end 620 of handle 602 and is defined in part by concave blade edge 612, widens therefrom toward mouth 614, opening at an included angle ranging from about 40° to about 60°. Point 618 extends laterally from blade segment 604 a substantially uniform distance to each side of blade segment 604 and comprises a body B having a leading edge LE, a slightly convex upper, proximal surface US and a similarly rounded lower, distal surface LS, as viewed from the side (FIG. 6B). Leading edge LE of point 618 is rounded at a small radius of curvature in side elevation (FIG. 6B) and in frontal elevation (FIG. 6C) is substantially linear with rounded edges extending to the side surfaces of body B. Point 618 protrudes at an included acute angle to longitudinal axis L of handle 602 of between about 45° and about 75°, for example about 60°, and is oriented toward proximal end 620 of handle 602. Notably, body B is connected to handle 602 only via blade segment 604, which extends from blade edge 612 to an opposing side of handle 602 and forms, in side elevation, a rounded distal end 606 which extends to body B. As blade segment 604 is thinner than handle 602 and point 618, a channel 616 extending from blade edge 612 to distal end 606 exists on each side of blade segment 604 between handle 602 and point 618. A boundary between handle 602 and a proximal side of blade segment 604 adjacent to handle 602 lies at an included angle to longitudinal axis L of between about 20° and about 50°, for example about 30°, widening channels 616 as they extend away from the blade edge 612. Proximal end 620 of handle 602 is also rounded in side elevation. The rounded lower surface LS of body B is slightly longitudinally offset from distal end 606 of blade 604, and the trailing edge of body B met by distal end 606 of blade segment 604 is rounded, both as depicted in FIG. 6B. Spine 622 at the back of handle 602 is substantially linear, while the front of handle 602 above recess 610 comprises an arcuate belly 624 bulging outwardly at one side of recess 610 and which recedes into a shallow concavity 626 substantially leading to rounded proximal end 620. Sides 628 of handle 602 are substantially flat, and the transitions between sides 628 and each of distal end 606, proximal end 620 and spine 622 of handle 602 are rounded and devoid of sharp edges. The transition surfaces from each side 628 of handle 602 to meet the sides of blade segment 604 within recess 610 above body B are also rounded and devoid of sharp edges. Upper, proximal surface US of body B meets the sides of blade segment 604 at the lower boundary of channels 616 at a substantially perpendicular angle. A side 628 of handle 602 may bear measurement increments in the form of a rule RL.

In the various embodiments of the surgical instrument of the present disclosure, after an initial incision is made in the tissue to be severed, for example the uterine wall, the surgical instrument is drawn toward the surgeon to lengthen the incision or to make additional incisions contiguous with the first incision.

In use of the first embodiment, depicted in FIGS. 1A through 1D, handle 102 of surgical instrument 100 is grasped by the hand of the surgeon about longitudinal axis L, point 118 is oriented downward by the surgeon to make a first incision, and then handle 102 of surgical instrument 100 is rotated upwardly so that point 118 is oriented substantially parallel to a path of intended elongation of the first incision. Surgical instrument 100 is then drawn toward the surgeon with point 118 below the tissue to be incised, so that the tissue is drawn into recess 110 and against blade edge 112, maintaining the tissue substantially within a plane defined by the depth of recess 110. The lower edge of arcuate belly 124 adjacent recess serves to limit the depth of the incision, while point 118 may serve to support the tissue being incised from the underside thereof.

In use of the second embodiment, depicted in FIGS. 2A through 2D, handle 202 of surgical instrument 200 is grasped by the hand of the surgeon about longitudinal axis L, point 218 is oriented downward by the surgeon to make a first incision, and then handle 202 of surgical instrument 200 is rotated upwardly so that point 218 is oriented substantially parallel to a path of intended elongation of the first incision. Surgical instrument 200 is then drawn toward the surgeon with point 218 below the tissue to be incised, so that the tissue is drawn into recess 210 and against blade edge 212, maintaining the tissue substantially within a plane defined by the depth of recess 210. The lower edge of arcuate belly 224 adjacent recess serves to limit the depth of the incision, while upper surface US of laterally extending, plow-shaped body P of point 218 may be used to support and even lift the tissue being incised to prevent damage to any underlying tissue, or the baby.

In use of the third embodiment, depicted in FIGS. 3A through 3D, point 318 is oriented downward by the surgeon to make a first incision, and then handle 302 of surgical instrument 300 is rotated upwardly so that point 118 is oriented substantially parallel to a path of intended elongation of the first incision. Surgical instrument 100 is then drawn toward the surgeon with point 318 below the tissue to be incised, so that the tissue is drawn into recess 310 and against blade edge 312, maintaining the tissue substantially within a plane defined by the depth of recess 310. Unlike in the case of the first and second embodiments, wherein handle 102, 202 may be grasped about longitudinal axis L by the hand of the surgeon, in the third embodiment the surgeon's index finger may be extended through aperture 330 to facilitate guidance and application of force to handle 302 to elongate the first incision as the remaining three fingers and thumb grip handle 302. Notably, exposed blade edge 312 is arcuate, and blade 304 is sized, and positioned with respect to axle A, so that tissue is drawn between convex blade edge 312 and point 318, and blade 304 rotates in a clockwise direction (as surgical instrument 300 is depicted in FIG. 3B), enhancing the cutting action of blade edge 312 by application of downward as well as lateral force. In a variation of the third embodiment, and as noted above, drive wheel or wheels W pressed against the exposed surface of the tissue being incised may cause positive blade rotation and, thus, an enhanced cutting action for blade 312. Point 318 may serve to support the tissue being incised from the underside thereof.

In use of the fourth embodiment, depicted in FIGS. 4A through 4D, handle 402 of surgical instrument 400 is grasped by the hand of the surgeon about longitudinal axis L, point 418 is oriented downward by the surgeon to make a first incision, and then surgical instrument 400 is rotated upwardly so that point 418 is oriented substantially parallel to a path of intended elongation of the first incision. Surgical instrument 400 is then drawn toward the surgeon with point 418 below the tissue to be incised, so that the tissue is drawn into recess 410 and against blade edge 412, maintaining the tissue substantially within a plane defined by the depth of recess 410. The lower edge of arcuate belly 424 adjacent recess serves to limit the depth of the incision, while point 418 may serve to support the tissue being incised from the underside thereof. Ridges R on spine 422 of handle 402 may enhance the surgeon's grip on surgical instrument 400.

In use of the fifth embodiment, depicted in FIGS. 5A through 5D, handle 502 of surgical instrument 500 is grasped by the hand of the surgeon, point 521 at proximal end 520 of handle 502 is oriented downward by the surgeon to make a first incision, and then surgical instrument 500 is reversed in the surgeon's hand so that point 518 is oriented substantially parallel to a path of intended elongation of the first incision and toward the surgeon. Surgical instrument 500 is then drawn toward the surgeon with point 518 below the tissue to be incised, so that the tissue is drawn into recess 510 and against blade edge 512, maintaining the tissue substantially within a plane defined by the depth of recess 510. The lower edge of arcuate belly 524 adjacent recess serves to limit the depth of the incision, while point 518 may serve to support the tissue being incised from the underside thereof.

In use of the sixth embodiment, depicted in FIGS. 6A through 6E, handle 602 of surgical instrument 600 is grasped by the hand of the surgeon about longitudinal axis L, point 618 is oriented downward by the surgeon to make a first incision, and then handle 602 of surgical instrument 600 is rotated upwardly so that point 618 is oriented substantially parallel to a path of intended elongation of the first incision. Surgical instrument 600 is then drawn toward the surgeon with point 618 below the tissue to be incised, so that the tissue is drawn into recess 610 and against blade edge 612, maintaining the tissue substantially within a plane defined by the depth of recess 610. The lower edge of arcuate belly 624 adjacent recess 610 serves to limit the depth of the incision, while slightly convex upper, proximal surface US of laterally extending body B of point 618 may be used to support and even lift the tissue being incised to prevent damage to any underlying tissue, or the baby. Surprisingly, the use of integral blade segment 604 with its unsharpened blade edge 612, does not hinder the tissue incision process to an unacceptable degree. Further, channels 616, which widen as they progress away from blade edge 612, facilitate movement of the incised tissue past surgical instrument 600 by eliminating any substantial barrier to passage of the incised tissue as surgical instrument 600 is drawn against fresh, unincised tissue during a procedure.

While the first, second, fourth and fifth embodiments are depicted with a substantially linear blade edge, it is also contemplated, as depicted in broken lines in FIG. 1B, that a blade edge 112' may be arcuate and concave in, so as to draw the tissue being incised toward the deepest portion of the concavity for enhanced cutting and control of the tissue. Similarly, the edge of integral blade segment of the sixth embodiment is arcuate and concave in shape.

It is also contemplated that the surgeon's grip on the handle of one or more of the embodiments illustrated and described herein may be enhanced with a scalloped protrusion SCP on the spine, such as is depicted in broken lines in FIG. 2B.

It is contemplated that any of the embodiments of the surgical instrument of the present disclosure may be made disposable in their entirety.

It is further contemplated that the distal portion of any of the embodiments 100, 200, 300, 400, 500 and 600 of the surgical instrument of the present disclosure may be made detachable from the proximal and intermediate portions of the handle along a boundary as shown by broken lines B in FIGS. 1B, 2B, 3B, 4B and 5B. In such a manner, not only can only the distal, blade-carrying portion of the surgical instrument be made disposable if desired, but a particular handle configuration favored by and familiar to the surgeon using the surgical instrument may be retained. The distal portion may be made removable by a cooperative "snap-fit" arrangement, by cooperative, aligned apertures through the intermediate and distal portions of the handle through which a fastener may be secured, by a dovetail and slot arrangement between the distal portion and the remainder of the handle, or through an aperture and key design wherein a projecting key in one of the intermediate portion of the handle and the distal portion is inserted in an aperture in the other of the intermediate portion and the distal portion, after which the two portions are mutually rotated to lock them together. Thus, a used and contaminated distal portion may be replaced for each procedure with a new, sterile distal portion carrying a sharp, unused blade.

While particular embodiments of the present disclosure have been shown and described, numerous variations and alternate embodiments, as well as different combinations of features from the various embodiments illustrated and described herein, will occur to those of ordinary skill in the art and are encompassed within the present disclosure. Accordingly, the scope of the present disclosure is limited only by the appended claims and their legal equivalents.

What is claimed is:

1. A surgical instrument, comprising:
an elongated handle;
a recess proximate a distal end of the elongated handle and facing at least partially toward a proximal end of the elongated handle;
a point oriented toward the proximal end of the elongated handle at an acute included angle to a longitudinal axis of the elongated handle and extending along a distal edge of the recess; and
a blade having an exposed blade edge facing a mouth of the recess;
wherein the blade is circular, and mounted for rotation to the elongated handle.

2. The surgical instrument of claim 1, wherein the acute included angle is about 60°.

3. The surgical instrument of claim 1, wherein the proximal end is one of rounded and pointed.

4. The surgical instrument of claim 1, wherein a protruding belly of the elongated handle extends along a proximal edge of the recess.

5. The surgical instrument of claim 1, wherein a base edge of the recess is arcuate.

6. The surgical instrument of claim 5, wherein the base edge is defined at least in part by the blade edge.

7. The surgical instrument of claim 1, wherein the point flares laterally to each side of the elongated handle.

8. The surgical instrument of claim 7, wherein the point is plow-shaped and comprises a rounded distal surface and a substantially flat proximal surface.

9. The surgical instrument of claim 7, wherein the point comprises a body having a convex proximal surface and a substantially linear, laterally extending, rounded leading edge.

10. The surgical instrument of claim 9, wherein the body has a convex distal surface and a rounded trailing edge.

11. The surgical instrument of claim 1, wherein the blade separates the point from the handle.

12. The surgical instrument of claim 11, wherein the blade comprises a blade segment integral with the handle and comprises a common, non-metal material with the handle.

13. The surgical instrument of claim 11, wherein a distance of separation between the handle and the point increases with distance from the blade edge.

14. The surgical instrument of claim 1, further comprising an aperture extending through the elongated handle proximate the distal end thereof.

15. The surgical instrument of claim 1, wherein the blade is mounted for rotation on an axle secured to the elongated handle.

16. The surgical instrument of claim 15, further comprising at least one drive wheel of a smaller diameter than a diameter of the blade and operably coupled to the axle proximate a side of the elongated handle.

17. The surgical instrument of claim 1, wherein the blade edge is inset from the mouth of the recess.

18. The surgical instrument of claim 1, further comprising measurement increments on the handle.

19. The surgical instrument of claim 18, wherein the measurement increments are located on one of a spine and a side of the handle.

20. The surgical instrument of claim 19, wherein the measurement increments are defined by ribs protruding from the spine.

21. The surgical instrument of claim 1, further comprising a gripping structure on a spine of the surgical instrument to enhance frictional engagement with digit of the user.

22. The surgical instrument of claim 21, wherein the gripping structure comprises a series of longitudinally spaced ribs on the spine.

23. The surgical instrument of claim 1, wherein the distal end of the handle carrying the blade is detachable from a remainder of the handle and replaceable by a like-configured distal portion.

24. A method of using a surgical instrument, the method comprising:
  perforating tissue in which an incision is to be made using a point on the surgical instrument; and
  elongating the perforation into an incision by drawing the surgical instrument toward the user;
  wherein using a point on the surgical instrument comprises using a point on a proximal end of the surgical instrument, and wherein elongating the perforation into an incision further comprises inserting another point on the surgical instrument proximate a distal end of the surgical instrument into the perforation, orienting the another point toward the user and drawing the another point toward the user to engage a blade of the surgical instrument with the tissue.

25. The method of claim 24, further comprising drawing the surgical instrument toward the user with a handle of the surgical instrument oriented at an angle of about 60° to a surface of the tissue.

26. The method of claim 24, further comprising drawing the surgical instrument toward the user to engage a blade of the surgical instrument with the tissue within a recess of the handle proximate a distal end thereof and defined between a point protruding from the handle and a portion of the handle.

* * * * *